United States Patent [19]

Lavielle et al.

[11] Patent Number: 5,162,324
[45] Date of Patent: Nov. 10, 1992

[54] NAPHYL PIPERAZINES USEFUL AS 5-HT$_{1A}$ RECEPTOR LIGANDS

[75] Inventors: Gilbert Lavielle, La Celle Saint-Cloud; Michel Laubie, Vaucresson; Francis Colpaert, Le Vesinet, all of France

[73] Assignee: Adir Et Compagnie, Courbevoie, France

[21] Appl. No.: 752,060

[22] Filed: Aug. 29, 1991

Related U.S. Application Data

[62] Division of Ser. No. 629,824, Dec. 19, 1990, Pat. No. 5,126,346.

[30] Foreign Application Priority Data

Dec. 20, 1989 [FR] France ............... 89 16882

[51] Int. Cl.$^5$ .................. A61K 31/495; C07D 401/00
[52] U.S. Cl. .................. 514/255; 514/252; 544/281; 544/360; 544/365; 544/367; 544/392; 544/393; 544/394; 544/395
[58] Field of Search .................. 544/365; 514/255

[56] References Cited

U.S. PATENT DOCUMENTS

| 4,335,126 | 6/1982 | Kleemann | 544/394 |
| 4,831,031 | 5/1989 | Lowe | 514/254 |
| 4,889,852 | 12/1989 | Hartog et al. | 514/230.5 |

FOREIGN PATENT DOCUMENTS

| 0279598 | 8/1988 | European Pat. Off. |
| 0281309 | 9/1988 | European Pat. Off. |
| 0372657 | 6/1990 | European Pat. Off. |

OTHER PUBLICATIONS

J. Med. Chem. 1989, 32, 1921-1926, Glennon et al.
Drug Development Research 16:335-343 (1989) Glennon et al.
Journal of Receptor Research 3(1-4), 59-81 (1988) Hoyer et al.
Collection Dzechoslov. Chem. Commun., vol. 40 (1975) pp. 1612-1622, Cervena et al.
J. Chem. Soc., 1963, pp. 1732-1738 Curd et al.
European Journal of Pharmacology, 160 (1989) 385-395, Lanbie et al.
European Journal of Pharmacology, 149 (1988) 213-223, Wouters et al.
TiPS, Dec. 1989 [124], vol. 10, No. 12, pp. cover, 470-471.
Neuropharmacology, vol. 28, No. 5, pp. 471-476 1989 Carli et al.
TiPS, May 1989, vol. 10, pp. 200-204, Saxena and Ferrari.
Pharmacology & Toxicology, 1989, 64 3-5 Ahlenius.
Drugs of the Future, 1988, pp. 429-439 Glaser.
Journal of Neural Transmisison, (1988) 74: pp. 195-198, Wadenburg.
J. Org. Chem. 1982, 47, pp. 3153-3163 Brown et al.
Recl. Trav. Chim. Pays-Bas 107, 303-309 (1988) Kruse et al.

*Primary Examiner*—Mukund J. Shah
*Assistant Examiner*—Matthew V. Grumbling
*Attorney, Agent, or Firm*—Gordon W. Hueschen

[57] ABSTRACT

Compounds of formula I:

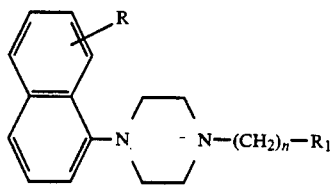

in which:
n=1-4,
R represents hydrogen, halogen, alkyl, hydroxyl or alkoxy, R$_1$ represents a radical —NHCOR$_2$ (A$_1$); (in which R$_2$ represents alkyl, cycloalkyl, phenyl optionally substituted-, -O-alkyl, 3-pyridyl, 2-pyrrolyl, quinolyl, 1-isoquinolyl, 2-thienyl or 3-indolyl); a radical of —NHSO$_2$R$_3$ (A$_2$) (in which R$_3$ represents alkyl, cycloalkyl or phenyl optionally substituted); a radical —NHCONHR$_4$ (A$_3$) (in which R$_4$ represents alkyl or phenyl-optionally substituted); a phthalimido radical (A$_4$); an o-sulfobenzoic imido radical (A$_5$); a di(benzoyl)amino radical (A$_6$) optionally substituted; a radical of formula A$_7$:

(in which R$_5$ represents carbamoyl, cyano, carboxy or alkoxycarbonyl); or a radical of formula A$_8$:

their stereoisomers and their addition salts with a pharmaceutically-acceptable inorganic or organic acid, are disclosed to be useful as 5-HT$_{1A}$ receptor ligands and accordingly as the active principle in medicinal products containing the same.

6 Claims, 1 Drawing Sheet

FIG. 1

NAPHYL PIPERAZINES USEFUL AS 5-HT$_{1A}$ RECEPTOR LIGANDS

The present application is a division of our prior-filed copending application Ser. No. 07/629,824, filed Dec. 19, 1990, now U.S. Pat. No. 5,126,346.

The present invention relates to new (1-naphthyl)piperazine compounds.

Some (1-naphthyl)-4-alkylpiperazine compounds having neuroleptic or antipsychotic properties are described in U.S. Pat. No. 4,831,031 and in Patent Applications EP 281,309 and EP 279,598. 1-[3-(3,4,5-Trimethoxyphenoxy)-2-hydroxypropyl]-4-arylpiperazine compounds having antiaggressive activity are described in U.S. Pat. No. 4,335,126. Arylpiperazine compounds having antagonist activity at the 5-HT$_{1A}$ receptor level are described in J. Med. Chem., (1989), 32, p. 1921–1926 and Drug Dev. Res., (1989), 16, p. 335–343. It is also known that (1-naphthyl)piperazine is a ligand of serotonin receptors (Journal of Receptor Research, (1988), (1-4), p. 59–81).

The compounds of the invention are distinguished from the other (1-naphthyl)piperazine compounds described in the literature by their novel structures and by their pharmacological properties.

At cardiovascular level, the compounds of the invention decrease arterial blood pressure and heart rate. This action results from central inhibition of sympathetic tonus and is linked with their 5-HT$_{1A}$ agonist properties. At central nervous system level, the compounds of the invention have demonstrated 5-HT$_{1A}$ agonist or antagonist properties. They can hence be useful in the treatment of migraine, depression, anxiety, schizophrenia, stress and pain.

The subject of the present invention is, more especially, the (1-naphthyl)piperazine compounds of general formula (I):

in which
n represents an integer from 1 to 4,
R represents a hydrogen atom, a halogen atom, an alkyl radical having 1 to 6 carbon atoms, a hydroxyl radical or an alkoxy radical having 1 to 6 carbon atoms,
R$_1$ represents a radical of formula A$_1$:

(in which
R$_2$ represents an alkyl radical having 1 to 6 carbon atoms, a cycloalkyl radical having 3 to 7 carbon atoms, a phenyl radical—optionally substituted with one or more halogen atoms, with one or more alkyl radicals having 1 to 6 carbon atoms or with one or more alkoxy radicals having 1 to 6 carbon atoms—an -O-alkyl radical having 1 to 6 carbon atoms, a 3-pyridyl radical, a 2-pyrrolyl radical, a quinolyl radical, a 1-isoquinolyl radical, a 2-thienyl radical or a 3-indolyl radical), a radical of formula A$_2$:

(in which R$_3$ represents an alkyl radical having 1 to 6 carbon atoms, a cycloalkyl radical having 3 to 7 carbon atoms or a phenyl radical—optionally substituted with one or more halogen atoms, with one or more alkyl radicals having 1 to 6 carbon atoms or with one or more alkoxy radicals having 1 to 6 carbon atoms), a radical of formula A$_3$:

(in which R$_4$ represents an alkyl radical having 1 to 6 carbon atoms or a phenyl radical optionally substituted with one or more halogen atoms or with one or more alkyl or alkoxy radicals having 1 to 6 carbon atoms), a phthalimide radical of formula A$_4$:

(with the proviso, however, that when n represents 4, R does not represent a hydrogen atom),
an o-sulfobenzoic imido radical of formula A$_5$:

or a radical of formula A$_6$:

(in which formulae X, Y and Z, which may be identical or different, each represent a hydrogen atom, a halogen atom, an alkyl radical having 1 to 6 carbon atoms or an alkoxy radical having 1 to 6 carbon atoms), or a radical of formula $A_7$:

$$R_5-\text{[imidazole-pyrimidine with CH}_3\text{, OH]}\quad(A_7)$$

(in which $R_5$ represents a carbamoyl radical, a cyano radical, a carboxy radical or an alkoxycarbonyl radical having 1 to 6 carbon atoms),
or a radical of formula $A_8$:

$$\text{[spirocyclic imide structure]}\quad(A_8)$$

their stereoisomers and their addition salts with a pharmaceutically acceptable inorganic or organic acid.

The subject of the present invention is also a process for preparing compounds of general formula I, wherein there is used as a starting material:

a/ either:
a compound of formula II:

$$\text{[naphthyl-piperazine with R]}\quad(II)$$

in which R has the same meaning as for the formula I,
which is condensed:
either
with a nitrile of formula III:

$$\text{Hal(CH}_2)_{n-1}\text{CN}\quad(III)$$

in which Hal represents a halogen atom and n has the same meaning as for the formula I, in an organic solvent, at room temperature, in the presence of an alkali metal salt, to obtain the compounds of formula IV:

$$\text{[naphthyl-piperazine-N-(CH}_2)_{n-1}\text{CN with R]}\quad(IV)$$

in which R and n have the same meaning as for the formula I, which is converted by means of lithium aluminum hydride or another equivalent chemical reagent
to a compound of formula V:

$$\text{[naphthyl-piperazine-N-C(CH}_2)_{n-1}\text{CH}_2\text{NH}_2\text{ with R]}\quad(V)$$

in which R and n have the same meaning as for the formula I,
which is reacted
either
with an equimolar quantity of a compound of formula $VI_A$ or $VI_B$:

$$\text{ClCOR}_2\quad(VI_A)$$

$$\text{ClSO}_2\text{R}_3\quad(VI_B)$$

in which $R_2$ and $R_3$ have the same meanings as for the formula I, to obtain, respectively, the compounds of formula I in which $R_1$ represents a radical of formula $A_1$ and the compounds of formula I in which $R_1$ represents a radical of formula $A_2$,
the compounds of formula I in which $R_2$ represents an -O-alkyl radical being reacted, if so desired, with a compound of formula VII:

$$R_4\text{NH}_2\quad(VII)$$

in which $R_4$ has the same meaning as for the formula I,
to form the compounds of formula I in which $R_1$ represents a radical of formula $A_3$,
or
with n excess of a compound of formula VIII:

$$\text{ClCO—[phenyl with X, Y, Z]}\quad(VIII)$$

in which X, Y and Z have the same meaning as for the formula I,
to form a compound of formula I in which $R_1$ represents a radical of formula $A_6$,
or
with a compound of formula $IX_A$ or $IX_B$:

$$\text{Hal—(CH}_2)_n\text{—N(CO)}_2\text{—[phenyl with X, Y, Z]}\quad(IX_A)$$

$$\text{Hal—(CH}_2)_n\text{—N(SO}_2\text{)(CO)—[phenyl with X, Y, Z]}\quad(IX_B)$$

in which Hal has the same meaning as for the formula III and X, Y and Z have the same meaning as for the formula I,
to form, respectively, the compounds of formula I in which $R_1$ is a radical of formula $A_4$ or a radical of formula $A_5$,
or
with an alcohol of formula X:

(X)

in which n has the same meaning as for the formula I and the meaning of Hal remains identical to that given for the formula III,
to form the compounds of formula XI:

(XI)

in which R and N have the same meaning as for the formula I,
which is subjected to the action of thionyl chloride or of another equivalent chemical reagent to form the compounds of formula XII:

(XII)

in which R and n have the same meaning as for the
which is condensed
either with ethyl acetoacetate to form a compound of formula XIII:

(XIII)

in which n and R have the same meaning as for the formula I,
which is condensed with a 4-aminoimidazole derivative of formula XIV:

(XIV)

in which $R_5$ has the same meaning as for the formula I,
to form the compounds of formula I in which $R_1$ represents a radical of formula $A_7$, or
with a compound of formula XV (XV)

to form the compounds of formula I in which $R_1$ represents a radical of formula $A_8$,
b/ or:
a compound of formula XVI:

(XVI)

in which R has the same meaning as in the formula which is condensed with N-benzyliminodiacetic acid of formula XVII, refluxed beforehand with carbonyldiimidazole in an anhydrous solvent such as tetrahydrofuran according to the technique described by C. G. KRUSE and J. J. TROST (Recueil des travaux chimiques des PaysBas, 107, 303–309, 1988)

(XVII)

to lead to a 2,6-piperazinedione of formula XVIII:

(XVIII)

in which R has the same meaning as in the formula I, on which a catalytic hydrogenation is carried out in the presence of palladinized charcoal as a catalyst, to lead to a 2,6-piperazinedione of formula XIX:

(XIX)

in which R has the same meaning as in the formula I, which is condensed
either with a nitrile of formula III:

Hal-(CH$_2$)$_{n-1}$-CN     (III)

in which Hal and n have the same meaning as above to lead to a 2,6-piperazinedione of formula XX:

in which R and n have the same meaning as in the formula I,
which is reduced in the presence of the borane/ dimethyl sulfide complex according to the technique described by H. C. BROWN et al. (J. Org. Chem., 47, 3153–3163, 1982)
to lead to a piperazine of formula V:

in which R and n have the same meaning as in the formula I,
which is reacted
either
with an equimolar quantity of a compound of formula VI$_A$ or VI$_B$:

ClCOR$_2$     (VI$_A$)

ClSO$_2$R$_3$     (VI$_B$)

in which R$_2$ and R$_3$ have the same meanings as for the formula I, to obtain, respectively, the compounds of formula I in which R$_1$ represents a radical of formula A$_1$ and the compounds of formula I in which R$_1$ represents a radical of formula A$_2$,
the compounds of formula I in which R$_2$ represents an -O-alkyl radical being reacted, if so desired, with a compound of formula VII:

R$_4$NH$_2$     (VII)

in which R$_4$ has the same meaning as for the formula I, to form the compounds of formula I in which R$_1$ represents a radical of formula A$_3$,
or
with an excess of a compound of formula VIII:

(VIII)

in which X, Y and Z have the same meaning as for the formula I,
to form a compound of formula I in which R$_1$ represents a radical of formula A$_6$,
or
with an alcohol of formula X:

Hal(CH$_2$)$_n$OH     (X)

in which Hal and n have the same meaning as above, to lead to a 2,6-piperazinedione of formula XXI:

in which R and n have the same meaning as in the formula I,
which is subjected to the action of thionyl chloride or of another equivalent chemical reagent,
to lead to a 2,6-piperazinedione of formula XXII:

in which R and n have the same meaning as in the formula I,
which is reduced in the presence of the borane/-dimethyl sulfide complex according to the technique described by H. C. Brown et al. (J. Org. Chem., 47, 3153–3163, 1982)
to lead to a piperazine of formula XII:

(XII)

in which R and n have the same meaning as in the formula I,
which is condensed
either
with a compound of formula XXIII$_A$, XXIII$_B$ or XV (XXIII$_A$)

-continued (XXIII$_B$)

(XV)

to lead, respectively, to the compounds of formula I in which R$_1$ is a radical A$_4$, A$_5$ and A$_8$,
or
with ethyl acetoacetate to form a compound of formula XIII (XIII)

in which n and R have the same meaning as for the formula I,
which is condensed with a 4-aminoimidazole derivative of formula XIV:

(XIV)

in which R$_5$ has the same meaning as for the formula I,
to form the compounds of formula I in which R$_1$ represents a radical of formula A$_7$,
which compounds of formula I are then,
if so desired, salified with a pharmaceutically acceptable organic or inorganic acid to form the corresponding addition salts.

The compounds of formula II are obtained according to the process described in Collection Czechoslov Chem. Commun., (1975), 40, p. 1612. The preparation of 1-(7-methoxy-1-naphthyl)piperazine is also known (J. Med. Chem., (1989), 32, No. 8, p. 1921).

The reaction of the compound of formula II with the compound of formula III is performed at room temperature, and preferably in the presence of potassium carbonate or sodium carbonate. The compounds of formula IV are converted to a compound of formula V at room temperature in an organic solvent, preferably tetrahydrofuran. The same working conditions are also used for the reaction of the compounds of formula V with the compounds of formula VI$_A$ or VI$_B$. The reaction is performed in the presence of triethylamine, and likewise the reaction of the compounds of formula V with the compounds of formula VIII.

The reaction of the compounds of formula VII with the compounds of formula I in which R$_2$ represents an -O-alkyl radical is described in J. Chem. Soc., (1949), p. 1732-1738.

Among the pharmaceutically acceptable acids for the preparation of addition salts with the compounds of general formula I, hydrochloric, phosphoric, fumaric, citric, oxalic, sulfuric, ascorbic, tartaric, maleic, mandelic and methanesulfonic acids, and the like, may be mentioned.

The compounds of the present invention possess highly advantageous pharmacological properties. At cardiovascular level, the compounds of the invention decrease arterial blood pressure and heart rate in rats and in dogs. This action results from a central inhibition of sympathetic tonus. In effect, pharmacological tests have shown that the fall in pressure caused by i.v. administration of the compounds of the invention in dogs is accompanied by a strong decrease in the electrical activity of the renal sympathetic nerve.

This central decrease in sympathetic tonus results from an activation of the central 5-HT$_{1A}$ receptors at the level of the retrofacial nucleus (Eur. Journal of Pharm., (1989), 160, p. 385-294). The pharmacological tests also showed that the compounds of the invention are approximately 3 times as active as flesinoxan, a reference compound having antihypertensive properties due to its 5-HT$_{1A}$ receptor agonist activity (European Journal of Pharmacology, (1988), 149, p. 213-223). Moreover, the compounds of the invention have a beneficial activity at renal level (T.I.P.S., (1989), 10, p. 469-471).

Binding tests confirmed that the compounds of the invention also behave as very potent ligands of 5-HT$_{1A}$ receptors, with an agonist or antagonist activity at central nervous system level.

The compounds of the invention hence find their application in the treatment of stress (Neuropharmac., (1989), Vol. 38, No. 5, p. 471-476), migraine (T.I.P.S., (1989), Vol. 10, pp. 200-204), anxiety, depression, schizophrenia and pain (Pharmacology and Toxicology, (1989), 64, p. 3-5), (Drugs of the Future, (1988), 13, No. 5, p. 429-437), (J. Neural. Transm., (1988), 74, p. 195-198).

The compounds active at 5-HT$_{1A}$ receptor level can also modify feeding and sexual behavior (Jour. of Receptor Research, (1988), 8, p. 59-81).

The invention also encompasses pharmaceutical compositions containing as active principle at least one compound of general formula I, or one of its salts with a pharmaceutically compatible inorganic or organic acid, in combination with one or more inert and suitable excipients.

The pharmaceutical compositions thereby obtained are advantageously presented in various forms such as, for example, tablets, dragées, hard gelatin capsules, suppositories, injectable solutions or solutions to be taken by mouth.

The dosage can vary widely in accordance with the patient's age and weight, the nature and severity of the condition and also the administration route. Generally speaking, the single doses will range between 0.05 and 10 mg, and the daily dosage usable in human therapy between 0.05 and 20 mg. The preferred administration route is the oral or parenteral route.

The examples which follow, given without implied limitation, illustrate the invention.

The melting points were measured according to the micro-Kofler technique.

The proton nuclear magnetic resonance ($^1$H NMR) or $^{13}$C carbon nuclear magnetic resonance ($^{13}$C NMR) spectra of the compounds of general formula I were recorded, depending on the case, at 200 and 400 MHz, and are shown in Table I.

EXAMPLE 1

1-(6-Methoxy-1-naphthyl)-4-[2-(4-fluorobenzoylamino)ethyl]piperazine hydrochloride

Stage A

1-Amino-6-methoxynaphthalene hydrochloride 19.5 g of 1-amino-6-hydroxynaphthalene are added in small quantities to a solution of sodium methanolate (2.82 g of sodium metal in 80 ml of methanol). The medium is stirred for one hour at room temperature and the solvent is then evaporated off under vacuum. The residue obtained is dissolved in 700 ml of acetone, and 9.27 g of dimethyl sulfate are added dropwise while a temperature below 60° C. is maintained. When the addition is complete, the medium is stirred for 12 hours at room temperature. The precipitate formed is filtered off, the filtrate is treated with active charcoal and the solvent is evaporated off under vacuum. The oil thereby obtained is purified by chromatography on 1 kg of 70–230 mesh silica using dichloromethane as eluent.

Yield: 55%.

Proton nuclear magnetic resonance spectrum (Solvent $CDCl_3$): 3.9 ppm, s, 3H; 4.1 ppm, 1H exchangeable; 6.6 ppm, dd, 1H; 7.0–7.3 ppm, m, 3H; 7.05 ppm, m, 1H; 7.65 ppm, d, 1H.

Stage B 1-(6-Methoxy-1-naphthyl)piperazine hydrochloride

A mixture of 4.1 g of the compound obtained in the preceding stage and 4.7 g of N,N-bis(chloroethyl)amine hydrochloride in 150 ml of chlorobenzene is brought to reflux for 24 hours. The precipitate is filtered off, washed with ether and recrystallized in ethanol to yield the expected product.

Yield: 70%.

Proton nuclear magnetic resonance spectrum (Solvent DMSO-$d_6$): 3.1–3.5 ppm, m, 8H; 3.9 ppm, s, 3H; 6.70 ppm, d, 1H; 7.15 ppm, m, 1H; 7.50 ppm, d, 1H; 7.8–7.5 ppm, m, 3H.

Stage C

[4-(6-Methoxy-1-naphthyl)piperazino]acetonitrile

A mixture of 5.8 g of the compound obtained in Stage B, 2.8 g of 2-bromoacetonitrile and 6.4 g of potassium carbonate in 250 ml of acetone is stirred at room temperature until the starting piperazine has completely disappeared, this being observed by TLC (eluent: dichloromethane/acetone 95:5 V/V). The medium is then filtered and the solvent evaporated off under vacuum. The product crystallizes in a minimum amount of ether.

Yield: 70%

| Elemental analysis: | C % | H % | N % |
|---|---|---|---|
| Calculated: | 72.57 | 6.81 | 14.93 |
| Found: | 72.44 | 7.01 | 14.67 |

Stage D 1-(6-Methoxy-1-naphthyl)-4-(2-aminoethyl)piperazine

A solution containing 4.2 g of the compound obtained in Stage C, in 25 ml of tetrahydrofuran is added dropwise at room temperature to a suspension, stirred under a nitrogen atmosphere, of 1.1 g of lithium aluminum hydride in 25 ml of tetrahydrofuran. Stirring is maintained for 20 minutes after the addition is complete, and the reaction medium is then hydrolyzed with the requisite quantity of water saturated with ammonium chloride. The precipitate formed is filtered off and washed with tetrahydrofuran, and the filtrates are concentrated under vacuum to yield an oil.

Yield: 74%.

Proton nuclear magnetic resonance spectrum (Solvent $CDCl_3$): 3.1–3.6 ppm, 4H; 3.1–4.0 ppm, m+m, 4+4H; 3.85 ppm, s, 3H; 7.0 ppm, d, 1H; 7.15 ppm, dd, 1H; 7.2–7.4 ppm, t+d, 1+1H; 7.6 ppm, d, 1H; 7.95 ppm, d, 1H.

Stage E 1.8 g of 4-fluorobenzoyl chloride in 50 ml of tetrahydrofuran are added to a solution, stirred at room temperature, of 3 g of the compound obtained in Stage D and 1.7 g of triethylamine in 20 ml of tetrahydrofuran. After contact for two hours, the reaction medium is filtered. The filtrate is concentrated under vacuum and the product obtained is crystallized in ether.

Yield: 76%.

Melting point: 180° C.

3.1 g of the base are dissolved in 300 ml of ethanol, and a requisite quantity of 6N methanolic hydrogen chloride is added dropwise. The hydrochloride precipitates.

Melting point: $\geq 260°$ C.

EXAMPLE 2

1-(6-Hydroxy-1-naphthyl)-4-[2-(4-fluorobenzoylamino)ethylpiperazine hydrochloride A solution of 0.85 g of the compound of Example 1, in base form, in 40 ml of dichloromethane is cooled to −20° C. under a nitrogen atmosphere 10 ml of a molar solution of boron tribromide in dichloromethane are then added dropwise while the temperature is maintained at −20° C. When the addition is complete, the medium is slowly heated to room temperature and stirred at this temperature for one hour before being hydrolyzed with 2 ml of ammonia solution. The organic phase, separated after settling has taken place, is dried over anhydrous magnesium sulfate and the solvent evaporated off under vacuum; the residue is dissolved in 20 ml of ethanol and the hydrochloride is precipitated by adding 0.4 ml of 6N ethanolic hydrogen chloride.

Yield: 72%.

Melting point: 216° C.

EXAMPLE 3

1-(7-Methoxy-1-naphthyl)-4-[2-(4-fluorobenzoylamino)ethyl]piperazine hydrochloride

Stage A

[4-(7-Methoxy-1-naphthyl)piperazino]acetonitrile

This compound is obtained from (7-methoxy-1naphthyl)piperazine according to the process described in Example 1, Stage C.

Yield: 74%.

Proton nuclear magnetic resonance spectrum (Solvent $CDCl_3$): 2.9 ppm, t, 4H; 3.2 ppm, t, 4H; 3.65 ppm, s, 2H; 3.95 ppm, s, 3H; 7.0–7.35 ppm, m, 3H; 7.5 ppm, m, 2H; 7.7 ppm, d, 1H.

Stage B 1-(7-Methoxy-1-naphthyl)-4-(2-aminoethyl)piperazine

This compound is obtained according to the method described in Example 1, Stage D, from [4-(7-methoxy-1-naphthyl)piperazino]acetonitrile.

Yield: 97%.

Proton nuclear magnetic resonance spectrum (Solvent DMSO-$d_6$): 3.1–3.55 ppm, m, 10H; 3.75 ppm, d, 2H; 3.95 ppm, s, 3H; 7.0–7.4 ppm, m, 3H; 7.4 ppm, d, 1H; 7.6 ppm, d, 1H; 7.85 ppm, d, 1H; 8.6 ppm, 1H exchangeable; 11.5 ppm, 1H exchangeable.

Stage C 1-(7-Methoxy-1-naphthyl)-4-[2-(4-fluorobenzoyl)aminoethyl]piperazine hydrochloride was obtained from the compound of the preceding stage according to the process described in Example 1, Stage E.

Yield: 40%.

Melting point: 221° C.

EXAMPLE 4

1-(7-Methoxy-1-naphthyl)-4-(2-[bis(4-fluorobenzoyl)amino]ethyl)piperazine hydrochloride To obtain this compound, the ether phase resulting during crystallization of the compound of Example 3 in base form is concentrated and chromatographed on 20 g of 70–230 mesh silica using a mixture of dichloromethane and acetone (95:5 V/V) as eluent.

Yield: 20%.

The base is then dissolved in isopropyl ether and converted to the hydrochloride with a solution of hydrochloric acid in diethyl ether.

Melting point: 234° C.

EXAMPLE 5

1-(7-Hydroxy-1-naphthyl)-4-2-(4-fluorobenzoylamino)ethylpiperazine hydrochloride This compound was prepared according to the process described in Example 2, from the compound of Example 3.

Yield: 80%.

Melting point: 230° C.

EXAMPLE 6

1-(7-Methoxy-1-naphthyl)-4-(2-tosylaminoethyl)piperazine hydrochloride

This compound was prepared according to the method described in Example 1, Stage E, from 1-(7-methoxy-1-naphthyl)-4-(2-aminoethyl)piperazine and tosyl chloride in solution in chloroform.

Yield: 44%.

Melting point: 277° C.

EXAMPLE 7

1-(7-Methoxy-1-naphthyl)-4-[2-(ethoxycarbonylamino)ethyl]piperazine hydrochloride This compound was prepared as indicated in the preceding example, from 1-(7-methoxy-1-naphthyl-)-4-(2aminoethyl)piperazine and ethyl chloroformate in chloroform.

Yield: 55%.

Melting point: 208° C.

EXAMPLE 8

1-(7-Methoxy-1-naphthyl)-4-(2-nicotinoylaminoethyl)piperazine hydrochloride

This compound was prepared according to the process described in Example 1, Stage E, from 1-(7-methoxy-1-naphthyl)-4-(2-aminoethyl)piperazine and nicotinoyl chloride.

Yield: 70%.

Melting point: 204° C.

EXAMPLE 5

1-(7-Hydroxy-1-naphthyl)-4-2-(4-fluorobenzoylamino)ethyl]piperazine hydrochloride This compound was prepared according to the process described in Example 2, from the compound of Example 3.

Yield 80%.

Melting point: 230° C.

EXAMPLE 6

1-(7-Methoxy-1-naphthyl)-4-(2-tosylaminoethyl)piperazine hydrochloride

This compound was prepared according to the method described in Example 1, Stage E, from 1-(7-methoxy-1-naphthyl)-4-(2-aminoethyl)piperazine and tosyl chloride in solution in chloroform.

Yield: 44%.

Melting point: 277° C.

EXAMPLE 7

1-(7-Methoxy-1-naphthyl)-4-[2-(ethoxycarbonylamino)ethyl]piperazine hydrochloride This compound was prepared as indicated in the preceding example, from 1-(7-methoxy-1-naphthyl)-4-(2aminoethyl)piperazine and ethyl chloroformate in chloroform.

Yield: 55%.

Melting point: 208° C.

EXAMPLE 8

1-(7-Methoxy-1-naphthyl)-4-(2-nicotinoylaminoethyl)piperazine hydrochloride

This compound was prepared according to the process described in Example 1, Stage E, from 1-(7-methoxy-1-naphthyl)-4-(2-aminoethyl)piperazine and nicotinoyl chloride.

Yield: 70%.

Melting point: 204° C.

EXAMPLE 9

1-(7-Methoxy-1-naphthyl)-4-[4-(4-fluorobenzoylamino)-1-butyl]piperazine hydrochloride

Stage A

4-[4-(7-Methoxy-1-naphthyl)piperazino]butyronitrile

This compound was prepared according to the process described in Example 1, Stage C, from 4-(7-methoxy-1-naphthyl)piperazine and 4-bromobutyronitrile.

Yield: 98%.

Proton nuclear magnetic resonance spectrum (Solvent CDCl$_3$): 1.85 ppm, m, 2H; 2.5 ppm, t, 2H; 2.6 ppm, t, 2H; 2.5–2.9 ppm, 4H; 3.1 ppm, 4H; 3.9 ppm, 3H; 7.10 ppm, d, 1H; 7.15 ppm, d, 1H; 7.25 ppm, t, 1H; 7.5 ppm, d, 1H; 7.55 ppm, s, 1H; 7.7 ppm, d, 1H.

Stage B 4-(7-Methoxy-1-naphthyl)-1-(4-amino-1-butyl)piperazine

This compound was prepared from the compound described in the preceding stage according to the process described in Example 1, Stage D.
Yield: 80%.

Stage C

The expected compound was prepared from 1-(7-methoxy-1-naphthyl)-4-(4-amino-1-butyl)piperazine and 4-fluorobenzoyl chloride.
Yield 60%.
Melting point: 224° C.

EXAMPLE 10

8-Carbamoyl-4-hydroxy-3-{2-[4-(7-methoxy-1naphthyl)piperazino]ethyl}-2-methylimidazo[1,5-a]pyrimidine hydrochloride

Stage A 2-4-(7-Methoxy-1-naphthyl)piperazino]ethanol hydrochloride

A mixture of 5 g of (7-methoxy-1-naphthyl)piperazine, 3.4 g of 2-iodoethanol and 5.5 g of potassium carbonate in 75 ml of acetonitrile is brought to reflux for 24 hours. The medium is then filtered and the solvent is evaporated off. The residue is purified by chromatography on 150 g of 70–230 mesh silica using a mixture of dichloromethane, methanol and ammonia solution (95:4.5:0.5 V/V) as eluent. The fractions containing the product are evaporated and the residue is dissolved in 20 ml of ethanol, then 2.1 ml of 6N ethanolic hydrogen chloride are added dropwise. The expected hydrochloride is obtained after precipitation with ether.
Yield: 70%.
Proton nuclear magnetic resonance spectrum (Solvent DMSO-$d_6$): 3.1–3.8 ppm, m+m, 2H+8H; 3.8–4.0 ppm, s+m, 3H+2H; 7.1–7.25 ppm, dd+d, 1H+1H; 7.3 ppm, t, 1H;, 7.4 ppm, d, 1H; 7.6 ppm, d, 1H; 7.85 ppm, d, 1H; 10.7–11.1 ppm, exchangeable complex.

Stage B 1-(7-Methoxy-1-naphthyl)-4-(2-chloroethyl)piperazine 3.6 g of thionyl chloride are added dropwise to a suspension containing 3.5 g of the compound obtained in the preceding stage in 100 ml of chloroform. When the addition is complete, the medium is heated to reflux for 1 hour 30 minutes. The precipitate is then filtered off and washed in the heated state in acetone.
Yield: 68%.
Melting point: 176° C.
Proton nuclear magnetic resonance spectrum (Solvent DMSO-$d_6$): 3.1–3.8 ppm, m, 10H; 3.9 ppm, s, 3H; 4.15 ppm, t, 2H; 7.0–7.4 ppm, d+t+dd+d, 1H+1H+1H+1H; 7.6 ppm, d, 1H; 7.85 ppm, d, 2H; 11.3–11.7 ppm, exchangeable complex.

Stage C

Ethyl 2-acetyl-4-[4-(7-methoxy-1-naphthyl)piperazino]butyrate hydrochloride 0.182 mol of ethyl acetoacetate is added at 0° C. to a suspension containing 0.182 mol of sodium hydride in 800 ml of tetrahydrofuran. The reaction medium is maintained for one hour at 20° C. and 0.182 mol of sodium iodide is then added. The mixture is cooled to 0° C. and 0.182 mol of the compound obtained in the preceding stage is added. The mixture is brought to reflux for 12 hours and then concentrated under vacuum. The residue is taken up in water and extracted with dichloromethane. The oil obtained is purified by chromatography on a column of 70–230 mesh silica, eluting with a mixture of dichloromethane and acetone (95:5 V/V).
Yield: 50%.
The ethyl 2-acetyl-4-[4-(7-methoxy-1-naphthyl)-piperazino]butyrate obtained is then diluted in ether, and the hydrochloride is precipitated after adding the requisite quantity of ethereal hydrogen chloride.
Proton nuclear magnetic resonance spectrum (Solvent CDCl$_3$): 1.3 ppm, t, 3H; 2.25–2.6 ppm, m+s, 2H+3H; 3.0–4.1 ppm, s+m+m+m, 3H+4H+6H+1H; 4.2 ppm, q, 2H; 7.1–7.35 ppm, 3H; 7.4 ppm, s, 1H; 7.6 ppm, dd, 1H; 7.8 ppm, d, 1H; 12.3–13.3 ppm, 1H exchangeable.

Stage D 0.01 mol of 4-amino-5-carbamoylimidazole hydrochloride, 0.011 mol of the ester prepared in the preceding step and 10.5 g of phosphoric acid are mixed. The mixture is brought to 80° C. for 30 minutes.
The mixture is hydrolyzed with ice and neutralized with concentrated sodium hydroxide to obtain the precipitation of 8-carbamoyl-4-hydroxy-3-{2-[4-(7-methoxy-1-naphthyl)piperazino]ethyl}-2-methylimidazo[1,5-a]-pyrimidine. The product is then salified with methanolic hydrogen chloride.
Yield 42%.
Melting point: 220° C.

EXAMPLE 11

8-Carbamoyl-4-hydroxy-2-methyl-3-{2-[4-(1-naphthyl)-piperazino]ethyl}imidazo[1,5-a]pyrimidine hydrochloride

Stage A 2-4-(1-Naphthyl)piperazino]ethanol hydrochloride

This compound was prepared from 2-iodoethanol and (1-naphthyl)piperazine according to the process described in Example 10, Stage A.
Yield: 85%.

Stage B 1-(1-Naphthyl)-4-(2-chloroethyl)piperazine

This compound was prepared from the product obtained in the preceding stage and according to the process described in Example 10, Stage B.
Yield: 50%.
Proton nuclear magnetic resonance spectrum (Solvent CDCl$_3$): 2.6–3.0 ppm, t+m, 2H+4H; 3.1 ppm, m, 4H; 3.7 ppm, t, 2H; 7.1 ppm, dd, 1H; 7.6–7.3 ppm, m, 4H; 8.2 ppm, m, 1H; 8.4 ppm, m, 1H.

Stage C

Ethyl 2-acetyl-4-4-(1-naphthyl)piperazino]butyrate hydrochloride

This compound was prepared according to the process described in Example 10, Stage C, from ethyl acetoacetate and 1-(1-naphthyl)-4-(2-chloroethyl)piperazine.
Yield: 40%.

Proton nuclear magnetic resonance spectrum (Solvent $CDCl_3$): 1.3 ppm, t, 3H; 2.0–2.3 ppm, m, 2H; 2.3 ppm, s, 3H; 2.45 ppm, t, 2H; 2.65 ppm, m, 4H; 3.1 ppm, m, 4H; 3.6 ppm, t, 1H; 4.2 ppm, g, 2H; 7.05 ppm, dd, 1H; 7.3–7.6 ppm, m, 4H; 7.8 ppm, m, 1H; 8.15 ppm, m, 1H.

Stage D

8-Carbamoyl-4-hydroxy-2-methyl-3-{2-[4-(1naphthyl)piperazino]ethyl}imidazo[1,5-a]pyrimidine hydrochloride was prepared from the ester obtained in the preceding stage and 4-amino-5-carbamoylimidazole according to the process described in Example 10, Stage D.

Yield: 30%.

Melting point: >260° C.

EXAMPLE 12

1-(7-Methoxy-1-naphthyl)-4-(2-phthalimidoethyl)piperazine hydrochloride

A mixture of 1.5 g of (7-methoxy-1-naphthyl)piperazine and 1.5 g of (2-bromoethyl)phthalimide in 100 ml of acetone is brought to reflux in the presence of 1.6 g of potassium carbonate. The mixture is stirred for 24 hours. The mixture is cooled, it is concentrated. The oil obtained is ground in ether. The requisite quantity of ethereal hydrogen chloride is added to obtain the expected hydrochloride.

Yield: 63%.

Melting point: 252° C.

EXAMPLE 13

1-(7-Methoxy-1-naphthyl)-4-[2-(2-thienoylamino)ethyl]piperazine hydrochloride

This compound was prepared according to the process described in Example 1, Stage E, from 1-(7-methoxy-1-naphthyl)-4-(2-aminoethyl)piperazine and 2-thiophenecarbonyl chloride.

Yield: 81%.

Melting point: 237° C.

EXAMPLE 14

1-(7-Methoxy-1-naphthyl)-4-[2-(4-fluorobenzoylamino)ethyl]piperazine hydrochloride

Stage A 1-(7-Methoxy-1-naphthyl)-4-benzyl-2,6-piperazinedione 126 mmol (2.2 equivalents) of carbonyldiimidazole are added to a suspension containing 58 mmol (1 equivalent) of N-benzyliminodiacetic acid in 200 ml of anhydrous tetrahydrofuran. The mixture is brought to reflux until the evolution of $CO_2$ has ceased. A solution containing 58 mmol (1 equivalent) of 1-amino-7-methoxynaphthalene in 40 ml of anhydrous tetrahydrofuran is then added to the above mixture. The resulting mixture is brought to reflux for 20 hours, the solvent is evaporated off and the residue obtained is taken up with 300 ml of anhydrous ethanol. The precipitate formed is filtered off and then dissolved in 200 ml of dichloromethane. The insoluble matter is filtered off and the filtrate concentrated. The expected product is then obtained after taking up in isopropyl ether followed by filtration.

Yield: 82%.

Melting point: 178° C.

Stage B 1-(7-Methoxy-1-naphthyl)-2,6-piperazinedione

A suspension containing 43 mmol of the product obtained in the preceding stage, stirred in the presence of 1 g of palladium on charcoal (10% Pd) in 500 ml of methanol, is hydrogenated at atmospheric pressure and at room temperature for 3 h 30 min. After filtration to remove the catalyst and evaporation of the solvent, the expected product is obtained.

Yield: 97%.

Melting point 232° C.

Stage C 1-(7-Methoxy-1-naphthyl)-4-(cyanomethyl)-2,6piperazinedione 11 mmol of the product obtained in the preceding stage are stirred at room temperature with 17 mmol of bromoacetonitrile and 13 mmol of triethylamine in 60 ml of an anhydrous acetone/anhydrous dimethylformamide (50:50) mixture. After hydrolysis with 200 ml of water, the expected product is obtained after filtering off the precipitate.

Yield: 64%.

Melting point: 204° C.

Stage D 1-(7-Methoxy-1-naphthyl)-4-(2-aminoethyl)piperazine 13 ml of a 2M solution (4 equivalents) of borane/dimethyl sulfide complex are added slowly to a solution containing 6.5 mmol (1 equivalent) of the product obtained in the preceding stage in 70 ml of anhydrous tetrahydrofuran at 60° C. The mixture is brought to reflux for 45 minutes while distilling off a dimethyl sulfide/ tetrahydrofuran mixture. The reaction volume is kept constant during this distillation by adding tetrahydrofuran. After hydrolysis at room temperature with 13.4 ml of 6N hydrochloric acid solution, the mixture is brought to reflux for 30 minutes.

The expected product is obtained after the addition of 54 ml of 2N sodium hydroxide, by extraction with 3 times 100 ml dichloromethane followed by chromatography on silica gel using a dichloromethane/methanol/ammonia solution (90:10:1) mixture as eluent.

Yield: 50%.

Stage E 1-(7-Methoxy-1-naphthyl)-4-[2-(4-fluorobenzoylamino)ethyl]piperazine hydrochloride The expected product is obtained as described in Stage C of Example; 3.

EXAMPLE 15

1-(7-Methoxy-1-naphthyl)-4-(2-butyrylaminoethyl)piperazine hydrochloride

Using the procedure described in Example 14, but replacing 4-fluorobenzoyl chloride in Stage E by butyryl chloride, the expected product is obtained.

Yield: 91%.

Melting point: 190° C.

| Elemental microanalysis: | | | | |
|---|---|---|---|---|
| | C % | H % | N % | Cl % |
| Calculated | 64.35 | 7.72 | 10.72 | 9.05 |

-continued

Elemental microanalysis:

|  | C % | H % | N % | Cl % |
|---|---|---|---|---|
| Found | 64.10 | 7.82 | 10.74 | 9.07 |

EXAMPLE 16

1-(7-Methoxy-1-naphthyl)-4-(2-cyclopropylcarbonylaminoethyl)piperazine hydrochloride Using the procedure described in Example 14, but replacing 4-fluorobenzoyl chloride in Stage E by cyclopropylcarbonyl chloride, the expected product is obtained.

Melting point: 204° C.

Elemental microanalysis:

|  | C % | H % | N % | Cl % |
|---|---|---|---|---|
| Calculated | 64.69 | 7.24 | 10.78 | 9.09 |
| Found | 64.48 | 7.58 | 10.68 | 8.86 |

EXAMPLE 17

1-(7-Methoxy-1-naphthyl)-4-[2-(4-fluorochenylsulfonamido)ethyl]piperazine hydrochloride Using the procedure described in Example 14, but replacing 4-fluorobenzoyl chloride in Stage E by 4-fluorobenzenesulfonyl chloride, the expected product is obtained.

Yield 79%.

Melting point: 229° C.

Elemental microanalysis:

|  | C % | H % | N % | Cl % | S % |
|---|---|---|---|---|---|
| Calculated | 57.55 | 5.67 | 8.75 | 7.39 | 6.68 |
| Found | 57.96 | 5.98 | 8.68 | 7.21 | 6.66 |

EXAMPLE 18

1-(7-Methoxy-1-naphthyl)-4-[2-(3-indolylcarboxamido)ethyl]piperazine hydrochloride Using the procedure described in Example 14, but replacing 4-fluorobenzoyl chloride in Stage E by 3-indolecarbonyl chloride, the expected product is obtained.

Yield: 67%.

Melting point: 242° C.

Elemental microanalysis:

|  | C % | H % | N % | Cl % |
|---|---|---|---|---|
| Calculated | 67.16 | 6.29 | 12.05 | 7.62 |
| Found | 67.04 | 6.45 | 11.96 | 7.72 |

EXAMPLE 19

1-(7-Methoxy-1-naphthyl)-4-2-(8-aza-7,9-dioxospiro[4.51]dec-8-yl)ethyl]piperazine hydrochloride Stages A and B are identical to those described in Example 10.

Stage C

A solution containing 0.49 g of 8-aza-7,9-dioxospiro[4.5]decane in 10 ml of dimethylformamide is added slowly to a suspension containing 0.13 g of 60% sodium hydride in 30 ml of dimethylformamide.

The mixture is brought to 70° C. for 30 minutes. After cooling, a solution containing 1 g of the product obtained in the preceding stage is added to the mixture and the resulting mixture is brought to reflux for 12 hours.

The expected product is obtained after evaporation, purification by chromatography on silica using a dichloromethane/acetone (90:10) mixture as elution solvent and precipitation of the hydrochloride in ethereal hydrogen chloride.

Yield: 60%.

Melting point: 216° C.

Elemental microanalysis:

|  | C % | H % | N % | Cl % |
|---|---|---|---|---|
| Calculated | 63.30 | 7.06 | 8.51 | 11.48 |
| Found | 63.66 | 7.06 | 8.27 | 11.74 |

TABLE I

NAPH

| EX. No | NAPH | n | R₁ | NMR spectrum (Solvent) |
|---|---|---|---|---|
| 1 | OCH₃ | 2 | —NH—CO—⟨C₆H₄⟩—F | (DMSO-d₆) s ¹H NMR 3.1–4.0 ppm, m+m, 4+8H; 3.85 ppm, s, 3H; 7.0 ppm, d, 1H; 7.15 ppm, dd, 1H; 7.2–7.5 ppm, t+t+d, 1+2+1H; 7.6 ppm, d, 1H; 7.95–8.1 ppm, dd+d, 2H+1H; 9.1 ppm, 1H exchangeable; 10.8–11.2 ppm, 1H exchangeable |

TABLE I-continued

| EX. No | NAPH | n | R₁ | NMR spectrum (Solvent) |
|---|---|---|---|---|
| 2 | 2-OH naphthyl (8-yl) | 2 | —NH—CO—C₆H₄—F (4-F) | (DMSO-d₆) s ¹H NMR 3.0–3.6 ppm, m, 8H; 3.6–3.85 ppm, m, 4H; 6.9 ppm, d, 1H; 7.0–7.2 ppm, m, 2H; 7.2–7.5 ppm, t+d+t, 1+1+2H; 7.9–8.1 ppm, d, 1H; 9.0 ppm, 1H exchangeable; 9.8 ppm, 1H exchangeable; 10.7 ppm, 1H exchangeable |
| 3 | 2-OCH₃ naphthyl (8-yl) | 2 | —NH—CO—C₆H₄—F | (DMSO-d₆) s ¹H NMR 3.1–3.6 ppm, m, 8H; 3.6–3.85 ppm, m, 4H; 3.9 ppm, s, 3H; 7.1–7.45 ppm, m, 6H; 7.6 ppm, d, 1H; 7.85 ppm, d, 1H; 8.05 ppm, dd, 2H; 9.0 ppm, 1H exchangeable; 10.95 ppm, 1H exchangeable |
| 4 | 2-OCH₃ naphthyl (8-yl) | 2 | —N(CO—C₆H₄—F)₂ | (DMSO-d₆) s ¹H NMR 3.1–3.85 ppm, m, 10H; 3.9 ppm, s, 3H; 4.45 ppm, m, 2H; 7.0–7.2 ppm, dd+d+t, 1+1+4H; 7.3 ppm, t, 1H; 7.4 ppm, d, 1H; 7.65 ppm, d+dd, 1+4H; 7.85 ppm, d, 1H; 10.9–11.2 ppm, 1H exchangeable |
| 5 | 3-OH naphthyl (8-yl) | 2 | —NH—CO—C₆H₄—F | (DMSO-d₆) s ¹H NMR 3.2–3.55 ppm, m, 8H; 3.8 ppm, m, 4H; 7.05 ppm, dd, 2H; 7.1–7.4 ppm, m, 4H; 7.5 ppm, d, 1H; 7.75 ppm, d, 1H; 8.1 ppm, dd, 2H |
| 6 | 2-OCH₃ naphthyl (8-yl) | 2 | —NH—SO₂—C₆H₄—CH₃ | (DMSO-d₆) s ¹H MNR 2.4 ppm, s, 3H; 3.1–3.8 ppm, m, 12H; 3.9 ppm, s, 3H; 7.15 ppm, d, 1H; 7.20 ppm, dd, 1H; 7.30 ppm, t, 1H; 7.40 ppm, d, 1H; 7.45 ppm, d, 2H; 7.60 ppm, d, 1H; 7.75 ppm, d, 2H; 7.8 ppm, d, 1H; 8.1 ppm, 1H exchangeable; 10.9–11.2 ppm, 1H exchangeable |
| 7 | 2-OCH₃ naphthyl (8-yl) | 2 | —NH—COOC₂H₅ | (DMSO-d₆) s ¹H NMR 1.2 ppm, t, 3H; 3.1–3.75 ppm, m, 10H; 3.7–4.0 ppm, s+m, 3+2H; 4.05 ppm, q, 2H; 7.1–7.25 ppm, dd+d, 1+1H; 7.3 ppm, t, 1H; 7.40 ppm, d, 1H; 7.50 ppm, 1H exchangeable; 7.65 ppm, d, 1H; 7.85 ppm, d, 1H; 11 ppm, 1H exchangeable |

TABLE I-continued

NAPH

| EX. No | NAPH | n | R₁ | NMR spectrum (Solvent) |
|---|---|---|---|---|
| 8 | 2-OCH₃, 1- (naphthyl) | 2 | —NH—CO—(3-pyridyl) | (DMSO-d₆) $\underline{s}$ ¹H NMR 3.1–4.0 ppm, $\underline{m}$+$\underline{m}$, 2+10H; 7.1–7.25 ppm, $\underline{m+m}$, 1+1H; 7.3 ppm, $\underline{t}$, 1H; 7.4 ppm, $\underline{d}$, 1H; 7.6 ppm, $\underline{d}$, 1H; 7.8 ppm, $\underline{m}$, 1H; 7.82 ppm, $\underline{d}$ 1H; 8.65 ppm, $\underline{d}$, 1H; 8.9 ppm, $\underline{dd}$, 1H; 9.3 ppm, $\underline{d}$, 1H; 9.5 ppm, 1H exchangeable; 11.0–11.3 ppm, 1H exchangeable |
| 9 | 2-OCH₃, 1- (naphthyl) | 4 | —NH—CO—(4-F-phenyl) | (DMSO-d₆) $\underline{s}$ ¹H NMR 1.5–1.7 ppm, $\underline{m}$, 2H; 1.7–2.0 ppm, $\underline{m}$, 2H; 3.1–3.5 ppm, $\underline{m}$, 10H; 3.6 ppm, $\underline{m}$, 2H; 3.65 ppm, 1H exchangeable; 3.9 ppm, $\underline{s}$, 3H; 7.05–7.40 ppm, $\underline{d+t+t+dd+d}$, 1H+2H+1H+1H+1H; 7.6 ppm, $\underline{d}$, 1H; 7.85 ppm, $\underline{d}$, 1H; 7.95 ppm, $\underline{dd}$, 2H; 10.6–11.0 ppm, 1H exchangeable |
| 10 | 2-OCH₃, 1- (naphthyl) | 2 | imidazole-CONH₂/OH/CH₃ substituent | (DMSO-d₆) $\underline{s}$ ¹H NMR 2,6 ppm, $\underline{s}$, 3H; 2.9–3.6 ppm, $\underline{m}$, 10H; 3.75 ppm, $\underline{m}$, 2H; 3.9 ppm, $\underline{s}$, 3H; 7.1–7.25 ppm, $\underline{m}$, 2H; 7.25 ppm, 1H exchangeable; 7.3 ppm, $\underline{t}$, 1H; 7.40 ppm, $\underline{d}$, 1H; 7.45 ppm, exchangeable; 7.6 ppm, $\underline{d}$, 1H; 7.85 ppm, $\underline{d}$, 1H; 8.15 ppm, $\underline{s}$, 1H; 10.8 ppm, 1H exchangeable, 11.65 ppm, 1H exchangeable |
| 11 | 1-(naphthyl) | 2 | imidazole-CONH₂/OH/CH₃ substituent | (DMSO-d₆) $\underline{s}$ ¹³C NMR 17.3 ppm; 19.5 ppm; 49.4 ppm; 51.3 ppm; 53.9 ppm; 100.1 ppm; 115.0 ppm; 115.1 ppm; 123.1 ppm; 123.5 ppm; 123.9 ppm; 125.7 ppm; 125.8 ppm; 126.0 ppm; 127.8 ppm; 128.3 ppm; 132.5 ppm; 134.2 ppm; 147.6 ppm; 151.4 ppm; 155.8 ppm; 164.3 ppm |
| 12 | 2-OCH₃, 1- (naphthyl) | 2 | phthalimido | (DMSO-d₆) $\underline{s}$ ¹H NMR 3.1–3.3 ppm, $\underline{s}$, 2H; 3.3–3.65 ppm, $\underline{m}$, 6H; 3.75 ppm, $\underline{m}$, 2H; 3.9 ppm, $\underline{s}$, 3H; 4,1 ppm, $\underline{t}$, 2H; 7.15 ppm, $\underline{d}$, 1H; 7.20 ppm, $\underline{dd}$, 1H; 7.30 ppm, $\underline{t}$, 1H; 7.4 ppm, $\underline{d}$, 1H; 7.6 ppm, $\underline{d}$, 1H; 7.8–8.0 ppm, $\underline{m+d}$, 4H+1H; 10.9–11.2 ppm, exchangeable complex |

TABLE I-continued

| EX. No | NAPH | n | R₁ | NMR spectrum (Solvent) |
|---|---|---|---|---|
| 13 | OCH₃ (naphthyl) | 2 | —NHCO—(thienyl) | (DMSO-d₆) $\underline{s}$ ¹H NMR 3.1–3.9 ppm, $\underline{m}$, 12H; 3.9 ppm, $\underline{s}$, 3H; 7.1–7.5 ppm, $\underline{dd+d+m}$, 1H+1H+1H; 7.30 ppm, $\underline{t}$, 1H; 7.4 ppm, $\underline{d}$, 1H; 7.60 ppm, $\underline{d}$, 1H; 7.80 ppm, $\underline{d}$, 1H; 7.85 ppm, $\underline{d}$, 1H; 7.95 ppm, $\underline{d}$, 1H; 9.1 ppm, exchangeable complex; 11 ppm, exchangeable complex |

$\underline{s}$ = salt
$\underline{b}$ = base

PHARMACOLOGICAL STUDY

EXAMPLE 20

Evaluation of the antihypertensive activity of the compounds of the invention

Mongrel dogs (male and female) are anesthetized with phenobarbital (30 mg/kg i.v.) and then placed in artificial respiration (Bird Mark VII respirator). Arterial blood pressure is measured by means of a catheter placed in the abdominal aorta via the femoral artery. This catheter is connected to a pressure cell (Statham ® R₂₃D₆) linked to a recorder.

Heart rate is measured by means of a Gould Biotach ®.

Sympathetic nervous activity is recorded from the renal nerve by means of a silver electrode. The amplified signal is visualized on an oscilloscope (Tektronix 5115 ®) and then measured in μV by means of a Gould integrator. The compounds under examination are administered i.v. The results of the study are given in Table II.

TABLE II

| COMPOUNDS | DOSE μg/kg | EFFECT ON ARTERIAL BLOOD PRESURE (mm/Hg) | EFFECT ON HEART RATE (Beats/min.) |
|---|---|---|---|
| Flesinoxan, (+) isomer | 10 | ↘ #10 | ↘ #15 |
|  | 30 | ↘ 10–25 | ↘ 15–25 |
|  | 100 | ↘ >30 | ↘ >40 |
| Flesinoxan, racemic | 10 | 0 | 0 |
|  | 30 | ↘ #10 | 0 |
|  | 100 | ↘ 10–25 | ↘ #15 |
|  | 300 | ↘ >30 | ↘ 15–25 |
| EXAMPLE 3 | 3 | ↘ #10 | ↘ #15 |
|  | 10 | ↘ 10–25 | ↘ 15–25 |
|  | 30 | ↘ >30 | ↘ 30–40 |
| EXAMPLE 5 | 3 | ↘ #10 | ↘ #15 |
|  | 10 | ↘ 10–25 | ↘ 30–40 |
|  | 30 | ↘ 10–25 | ↘ 30–40 |
| EXAMPLE 13 | 1 | ↘ #10 | ↘ 15–25 |
|  | 3 | ↘ 10–25 | ↘ 15–25 |
|  | 10 | ↘ >30 | ↘ 15–25 |

The results shown in Table II demonstrate that the compounds of the invention are approximately 3–10 times as potent as the reference product flesinoxan in racemic form or in the form of the (+) isomer. This isomer is the more active isomer of flesinoxan.

Figure 1:
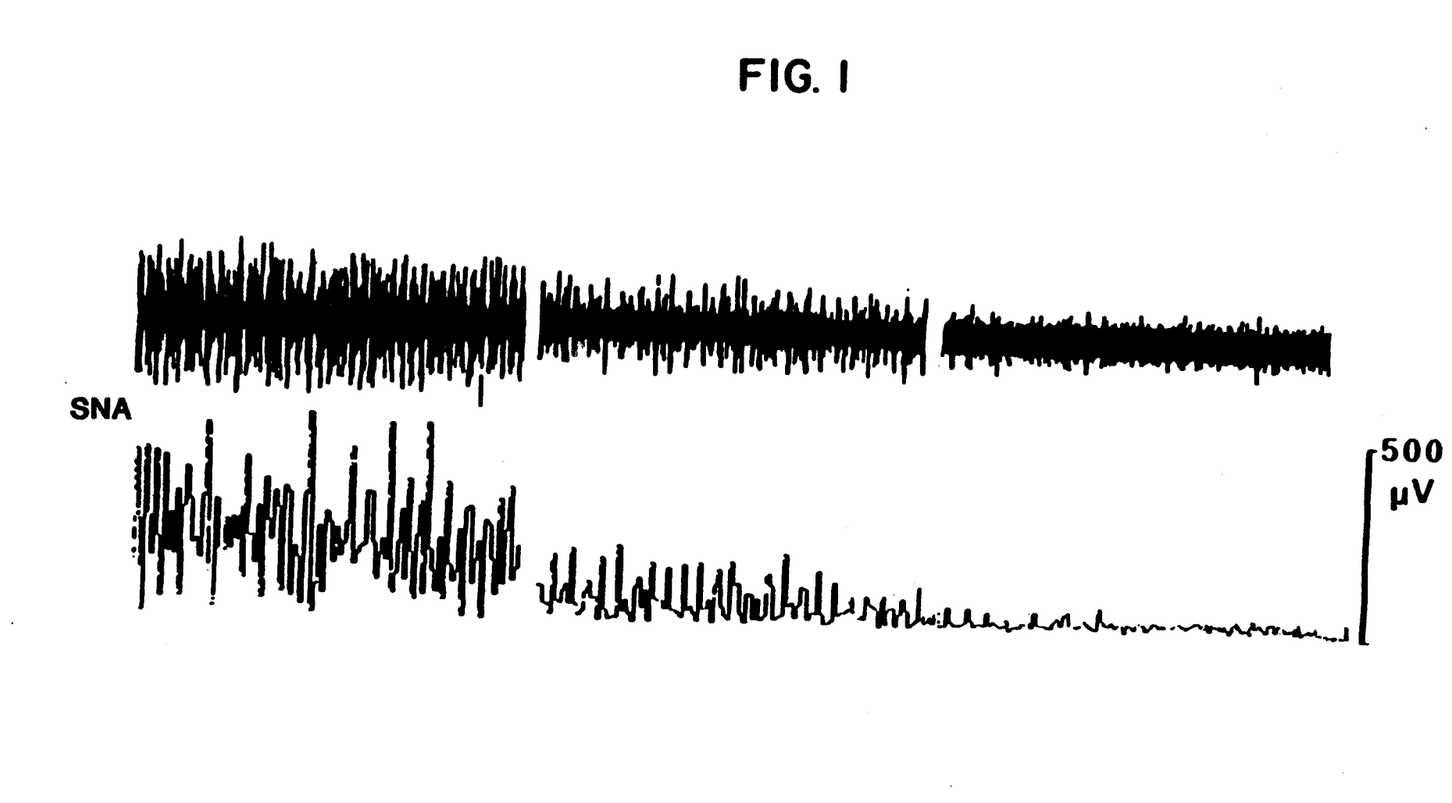
FIG. 1 is a graph and an amplified graph showing sympathetic nervous activity (SNA) as demonstrated for compounds of the invention according to Example 20.

As regards sympathetic nervous activity, the results obtained with the compound of Example 3 after i.v. administration of a dose of 10 μg/kg are given in FIG. 1.

EXAMPLE 21

Evaluation of the affinity for 5-HT$_{1A}$ receptors

For the tests, hippocampal tissue obtained from decapitated Wistar rats was used. The animals were sacrificed 48 hours before the experiment and the isolated tissues were stored at −86° C. For the preparation of the membranes, the tissues were then homogenized using 20 volumes of 50 mM Tris-HCl buffer solution (pH 7.7 adjusted using NH₄Cl at 25° C.) for one volume of tissue, at a temperature in the region of 0° C., with a Polytron ® homogenizer, and the whole was then centrifuged (35,000 g×20 min at 4° C.). The pellet thereby obtained was suspended in 100 volumes of an incubation buffer solution (60 mM Tris, 10 μM pargyline, 4 mM CaCl₂ and 0.1% (w/v) ascorbic acid; pH adjusted to 7.7 with 5N HCl). The compounds under examination were also diluted in the incubation buffer, and the test solutions were then prepared by adding 100 μl of a solution of the compound under examination and 100 μl of a solution of [$^3$H]-8-OHDPAT, C=0.4 nM (specific radioactivity=205 Ci/mmol), into 12×75 mm glass tubes. Non-specific binding was determined by means of a 10 μM solution of 5-hydroxytryptamine, and corresponds to 5–10% of the total binding.

The tubes were incubated for 30 min at 37° C., and the solutions were then filtered through GF/B glass fiber filters treated with 0.1% polyethyleneimine (Whatman ®). The filters were rinsed twice with 5 ml of the incubation buffer solution and were then placed in vials into which 4.5 ml of "Picofluor scintillation fluid" ® (Packard) were added. The radioactivity was determined using external standards.

The pKi values were determined using the Cheung-Prusoff equation:

$$-\log (IC_{50}/[1+[^3H]-8-OH-DPAT]/Kd).$$

The compounds of the invention have a great affinity for 5-HT$_{1A}$ sites. The pKi values of the compounds of the invention are of the order of 9.01 nmol/liter.

PHARMACEUTICAL PREPARATION

EXAMPLE 22

Hard gelatin capsules containing a 1-mg dose of 1-(7-methoxy-1-naphthyl)-4-[2-(4-fluorobenzoylamino)-ethyl]piperazine hydrochloride [M.N.F.B.A.E.P.]

| | |
|---|---|
| M.N.F.B.A.E.P. | 1 mg |
| Maize starch | 15 mg |
| Lactose | 25 mg |
| Talc | 5 mg |

We claim:

1. A compounds selected from those of formula I:

in which:
n represents 1 to 4,
R represents hydrogen, halogen, alkyl having 1 to 6 carbon atoms, hydroxyl or alkoxy radical having 1 to 6 carbon atoms,
R$_1$ represents a radical of formula A$_1$:

in which R$_2$ represents a 3-pyridyl radical, its stereoisomers and its addition salts with a pharmaceutically-acceptable inorganic or organic acid.

2. A pharmaceutical composition useful for modifying 5-HT$_{1A}$ containing as active principle a compound as claimed in claim 1, in combination or mixed with a pharmaceutically-acceptable excipient or vehicle.

3. The pharmaceutical composition as claimed in claim 2, containing the active principle an effective 5-HT$_{1A}$ receptor-modifying amount of in amount of 0.05 to 10 mg.

4. A method for treating an animal or human living body afflicted with a condition involving 5-HT$_{1A}$ receptors selected from the group consisting of migraine, depression, anxiety, schizophrenia, stress, and pain, comprising the step of administering to the said living body an amount of a compound of claim 1 which is effective for alleviation of said condition.

5. A method for treating a living body afflicted with hypertension comprising the step of administering to the said living body an amount of a compound of claim 1 which is suitable for alleviation of said condition.

6. 1-(7-Methoxy-1-naphthyl)-4-(2-nicotinoylaminoethyl)piperazine or an addition salt thereof with a pharmaceutically-acceptable inorganic or organic acid.

* * * * *

UNITED STATES PATENT AND TRADEMARK OFFICE
CERTIFICATE OF CORRECTION

PATENT NO. : 5,162,324
DATED : Nov. 10, 1992
INVENTOR(S) : Gilbert Lavielle, Michle Laubie, Francis Colpaert, It is certified that error appears in the above-identified patent and that said Letters Patent is hereby corrected as shown below:

Title Page, column 1, [54] "NAPHYL" should read -- NAPHTHYL --.
Column 1, line 1; "NAPHYL" should read-- NAPHTHYL --.
Column 1, approximately line 21,22; "(1988, (1-4)," should read -- (1988, 8 (1-4), --
Column 4, line 39; "with n excess" should read --with an excess--.
Column 10, line 20; "p. 385-294" should read -- 385-394 --.
Column 12, line 11; "3.6 ppm, 4H;" should read --3.6 ppm, m, 4H;--.
Column 12, line 35; "ethylpiperazine" should read -- ethyl]piperazine --.
Column 12, line 39; "atmosphere 10" should read --atmosphere. 10--.
Column 12, approximately line 61; "(7-methoxy-1naph-" should read -- (7-methoxy-1-naph- --.
Column 12, line 66; "3.2 ppm, t, 4H;" should read --3.2 ppm, m, 4H;--.
Column 13, line 26; move the ")" from the beginning of line 26 to the end of line 25 and insert before the hyphen.
Column 13, line 26; "aminolethyl)" should read --amino]ethyl} --.
Column 13, line 40; "-4-2-" should read -- 4-[2- --.
Column 13, line 41; "ethylpiperazine" should read -- ethyl]piperazine --.
Column 13, line 61; "ethylpiperazine" should read -- ethyl]piperazine --.
Column 13, line 65;"(2aminoethyl)" should read--(2-aminoethyl)--.
Column 14; approximately lines 12-53, beginning with "EXAMPLE 5," and ending with "Melting point 204° C." at the end of EXAMPLE 8 ; delete this duplication of text.

Column 14, line 68; "2.5-2.9 ppm, 4H; 3.1 ppm, 4H; 3.9 ppm, 3H;" should read -- 2.5-2.9 ppm, m, 4H; 3.1 ppm, m, 4H; 3.9 ppm, 2, 3H; --
Column 15, line 20; "-1naph-" should read -- -1-naph- --.
Column 15, line 21; "piperazino ethyl)-2- should read -- piperazine]ethyl -2- --
Column 15, line 25; "2-4-" should read -- 2-[4- --.

UNITED STATES PATENT AND TRADEMARK OFFICE
CERTIFICATE OF CORRECTION

PATENT NO. : 5,162,324

DATED : Nov. 10, 1992

INVENTOR(S) : Gilbert Lavielle, Michle Laubie, Francis Colpaert

It is certified that error appears in the above-identified patent and that said Letters Patent is hereby corrected as shown below:

Column 16, approximately line 19; "ppm, 3H;" should read -- ppm, m, 3H; --.

Column 16, line 39; "piperazinolethyl" should read -- piperazine]ethyl --.

Column 16, line 39; "alpyrimidine" should read -- a]pyrimidine--.

Column 16, approximately line 44; "2-4-" should read --2-[4- --.

Column 16, line 44, "piperazinolethanol" should read -- piperazino]ethanol --.

Column 16, line 62; "-4-4-" should read -- -4-[4- --

Column 20, line 14; "-4-2-(8-" should read -- -4-[2-(8- --

Column 22, Example No. 7, 5th column, 3rd line; "g," should read -- q, --.

Column 27, last line; "compounds" should read -- compound --.

Column 28, line 13; "alkoxy radical having" should read -- alkoxy having --.

Column 28, approximately line 25; "5-HT$_{1A}$containing" should read -- "5-HT$_{1A}$ receptors containing --.

UNITED STATES PATENT AND TRADEMARK OFFICE
CERTIFICATE OF CORRECTION

PATENT NO. : 5,162,324
DATED : Nov. 10, 1992
INVENTOR(S) : Gilbert Lavielle, Michel Laubie, Francis Colpaert It is certified that error appears in the above-identified patent and that said Letters Patent is hereby corrected as shown below:

Column 28, approximately 25; "principle a compound" should read --principle an effective $5\text{-HT}_{1A}$ receptor-modifying amount of a compound --.

Column 28, approximately line 29/30; delete "an effective $5\text{-HT}_{1a}$ receptor-modifying amount of".

Col. 13, line 25, "-4-(2-" should read -- -4-{2- --.

Signed and Sealed this

Sixteenth Day of November, 1993

BRUCE LEHMAN

Attest:

Attesting Officer

Commissioner of Patents and Trademarks